United States Patent [19]

Goldberg

[11] 4,206,197

[45] Jun. 3, 1980

[54] CHEMICAL ENCAPSULATION AND DISTRIBUTION

[75] Inventor: Leonard J. Goldberg, Berkeley, Calif.

[73] Assignee: The United States of America as represented by the Secretary of the Navy, Washington, D.C.

[21] Appl. No.: 635,472

[22] Filed: Nov. 26, 1975

[51] Int. Cl.² ............................................ A01N 17/00
[52] U.S. Cl. ...................................... 424/38; 424/16; 424/282; 424/312; 424/DIG. 12
[58] Field of Search ............... 424/282, 312, DIG. 12, 424/31, 38, 16

[56] References Cited

U.S. PATENT DOCUMENTS

| | | | |
|---|---|---|---|
| 2,957,803 | 10/1960 | Woods | 424/354 |
| 3,184,380 | 5/1965 | Woods | 424/354 |
| 3,829,577 | 8/1974 | Chodnekar et al. | 424/DIG. 12 |
| 3,912,815 | 10/1975 | Henrick et al. | 424/DIG. 12 |

OTHER PUBLICATIONS

Schaefer et al., "Jour. of Econ. Ent.," vol. 66, #4 (1973), pp. 923–925.

*Primary Examiner*—V. D. Turner
*Attorney, Agent, or Firm*—R. S. Sciascia; Charles D. B. Curry; Francis I. Gray

[57] ABSTRACT

A method of coating chemicals that are used in the control of insects which protects the chemicals from biodegradation and improves their distribution in insect-containing bodies of water. A fat is mixed with an appropriate solvent, surfactant and chemical to be coated and is heated to a temperature at which relative homogeneity of the solution is achieved. When using a water miscible solvent, the mixture is pressure injected into a body of water as a fine mist under high pressure. A non-water-soluble solvent may be used; in such an instance a suitable solvent extracting process, such as spray drying, is undertaken before the introduction of the material into a body of water. A stable colloid containing the chemical is the final dispersion in a body of water.

6 Claims, No Drawings

CHEMICAL ENCAPSULATION AND DISTRIBUTION

BACKGROUND OF THE INVENTION

1. Field of the Invention.

The present invention relates to the preservation and improved effectiveness of chemicals used to kill or otherwise regulate the growth of undesirable living bodies in an aqueous environment. In particular, it relates to processes for applying a coating of fat to chemical growth regulators and insecticides.

2. Description of the Prior Art.

In the application of chemicals or biologicals to control insects, many of the chemicals employed are sensitive to biodegradation. The Zoecon growth regulator ZR-515 is an example. By a process of microencapsulation this chemical has been successfully protected from biodegradation (Zoecon SR-10). The control of particle size and density, however, is also required for optimal aquatic effectiveness.

This Zoecon process of microencapsulation was tried on a bacterial endotoxin without success, thus indicating the complexity of the problem since the encapsulation procedure utilized with success on one chemical was not effective in application on a second control agent.

Additionally, it has been found that chemicals having a density greater than one are inefficiently disbursed in the aquatic environment with which they are commonly confronted, namely a pond. Such chemicals will tend toward the lowest depths of such a pond, minimizing their concentration at the edges, the more likely breeding area of pests. Suspension of the chemicals throughout such a body of water is desirable.

Woods, in U.S. Pat. Nos. 2,957,803 and 3,184,380, has devised methods of suspending certain water insoluble pesticides. His processes rely critically upon agitation throughout the processes. The constant agitation of the Woods' processes inherently create field preparation complications.

The above processes require complex and expensive preparation. For example, Zoecon SR-10 contains only 10 percent active ingredients. The colloid must be mixed before leaving the factory, causing a multiplication of transportation costs and a reduction in field life.

The present invention protects certain growth regulators from biodegradation while improving their effectiveness by a process capable of efficient practice in the field which forms a stable colloid of chemical particles encapsulated by a fat.

SUMMARY OF THE INVENTION

The present invention basically provides a coating for chemicals adapted to attack pests in their water-borne states, such chemicals including Zoecon ZR-515 and Hoffman LaRoche RO-20-3600. A fat is mixed with an appropriate water miscible solvent, surfactant and chemical to be coated and is heated to a temperature at which relative homogeneity of the solution is achieved. The mixture is then pressure injected into the water body to be treated as a fine mist under high pressure. If a non water-soluble solvent has been used, a suitable solvent extracting process, such as spray drying, is applied before the injection of the material into the body of water. A stable colloid in which the coated chemical exists is formed in the body of water in which insect control is desired.

OBJECTS OF THE INVENTION

An object of this invention is to provide a method of prolonging the useful field life of an insecticide or growth regulator, such as Zoecon ZR-515 or Hoffman LaRoche RO-20-3600.

Another object of this invention is to provide a method of producing a stable colloidal suspension of a chemical such as one of those above-mentioned.

A further object of this invention is to achieve the above-named objects by a simplified and economical process.

Yet another object of this invention is to provide for effective activity of the encapsulated chemical following larval ingestion.

Other objects, advantages and novel features of the invention will become apparent from the following detailed description.

DESCRIPTION OF THE PREFERRED EMBODIMENT

The biodegradation that occurs to chemicals applied as growth regulators or insecticides to control pests in their water-borne stages is believed to result from the action of bacterial enzymes contained in water. It has been found that certain growth regulators may be economically and effectively coated by the process of this invention (described below) to protect the chemical from biodegradation, while at the same time providing for larvicidal activity following ingestion.

Growth regulators operate to interfere with the development stage transitions in various insects. Such stages are "triggered" by certain chemical signals. The growth regulator is designed to overwhelm such signals in the insect's system. Zoecon ZR-515 and Hoffman LaRoche RO-20-3600 interfere with the transition of pupal to adult stage. Other growth regulators may effect other transitions. Monsanto 585, which can rapidly form a surface slick in water if not modified by a suitable surfactant, interferes with the transition of larva to pupae. Thompson-Hayward 6040 interferes with the molting process in the larval stage.

The encapsulation process of the present invention is relatively simple, allowing the performance of a large percentage of the process at the application site, reducing transportation costs and increasing field life.

Also, the effectiveness of growth regulators and insecticides having a density greater than one against water-borne pests is minimized when such chemicals settle in areas of little pest activity. The creation of a substantially neutral density colloidal suspension of such chemicals is thus highly desirable.

As a first step in the process of the present invention a solvent is selected in which both the chemical to be coated and the coating fat are soluble, though not necessarily at the same temperatures. To this mixture a suitable surfactant is added. The surfactant acts in the process as a "glue" between the chemical and the encapsulating fat.

Upon mixture of the chemical, surfactant, fat and solvent, the temperature of the mixture is raised to the highest temperature required for solubility of any of the above-mentioned in the chosen solvent.

If the solvent is miscible in water, the mixture may be pressure injected into the body of water to be treated without a separate solvent removal step. Such is the case when the solvent employed is acetone.

Non water-soluble solvents such as chloroform require a solvent removal step such as spray drying prior to the injection of the encapsulated chemical into the pond or other body of water.

Upon removal of the solvent by appropriate means particles, each containing a nucleus of a selected chemical, are obtained which are entirely surrounded by an intermediate layer of surfactant joining this nucleus to an outer coating of fat. Following ingestion by the insect, the insect's digestive process removes the encapsulating fat, releasing the chemical within.

The following water insoluble pesticides have characteristics that fit them for the process:

| Common names: | Chemical names: |
|---|---|
| Zoecon ZR-515 | Isopropyl E, E-11-Methoxy-3, 7, 11-Triemthyl-2, 4 Dodecadienoate |
| Hoffman LaRoche RO-20-3600 | 6, 7-Epoxy-3, 7-Dimethyl-1-[3, 4-(Methylenedioxy)-Phenoxy]-2-Nonene |

The two above-named chemicals have been successfully encapsulated by processes within the scope of the present invention, hereinafter referred to respectively as Example I and Example II.

Example I

According to the invention a colloid of approximately neutral density in water was prepared by combining ZR-515, palm coating seeding crystal, Emplex and Acetone in approproximate proportions of 1:1:.1:19 by weight. (The chemical formula for EMPLEX is sodium stearoyl-2-lactylate, an emulsifier commonly used in the baking industry as a dough conditioner.)

Palm coating seeding crystal acts as the encapsulating fat. This fat has a density less than one and is soluble in acetone at a temperature of 120 degrees Farenheit. ZR-515 is acetone-soluble at room temperature.

Emplex acts as a surfactant for the above-named chemical and encapsulant.

The mixture is heated to 120 degrees Farenheit to assure homogeneity and full dissolution of all ingredients in the solvent.

It is maintained at at least 100 degrees then pressure injected into the water to be treated. It was found that, by pressure injecting the mixture through a 27 gauge needle under a nominal (hand) pressure a colloid was formed having a particle size of 0.1 to 1.0 microns. Such a small size is highly desirable and necessary. A particle greater than 10 microns in diameter may not be readily ingestible by some insect targets. Additionally, the fine size of the particles provides stability to the suspended colloid. The fact that the fat has a density less than one and the growth regulator a density greater than one allows adjustment of the colloid particles to neutral density and, hence, enhanced colloidal stability in water.

Example II

Hoffman LaRoche RO-20-3600 is a growth regulating chemical insoluble in water and having a density greater than one. It has been found that, as in the case of ZR-515, palm coating seeding crystal provides a successful encapsulant with Emplex as the surfactant.

Unlike ZR-515, RO-20-3600 is not soluble in acetone. The practice of the present invention to encapsulate RO-20-3600 requires the use of some other solvent such as chloroform. A solvent removal process is necessitated by the use of chloroform due to the water insolubility of chloroform.

The RO-20-3600, palm coating seeding crystal, Emplex and chloroform were combined in approximate proportions of 1:1:.1:19 by weight at 120 degrees Farenheit to assure dissolution of all ingredients into a homogeneous mixture.

The mixture went through a solvent removal process before being impinger sampled into a water environment. Pressure spray drying will remove the chloroform and impinger sampling will trap the resultant fine aerosol to provide a neutral density colloid within a body of water.

In view of the foregoing, it can be seen that a chemical encapsulation and distribution process has been achieved that protects from biodegradation certain chemicals used to control insects and pests while improving the effectiveness of such chemicals against such targets following ingestion by the target insect.

What is claimed is:

1. A process for protecting a water insoluble chemical, having a density greater than one and adapted to attack pests in their water-borne states, from biodegradation which comprises the steps of:
    (a) mixing a selected fat having a density less than one with said chemical in a solvent in which said fat and said chemical are both soluble, said fat being of sufficient amount in relation to said chemical to achieve neutral buoyancy in water when combined with said chemical, and said solvent being of sufficient amount in relation to said fat and said chemical to completely dissolve said fat and said chemical therein;
    (b) adding a selected surfactant, suitable for binding said fat to said chemical in said solvent, in an amount sufficient to completely bind said fat to said chemical;
    (c) heating said mixture to the minimum temperature necessary for the dissolution of said fat, chemical and surfactant in said solvent; and
    (d) removing said solvent from said mixture to form a colloidal solution of fine particles of fat encasing said chemical.

2. A process as described in claim 1 wherein:
    (a) said chemical is isopropyl 11-methoxy-3,7,11-trimethyl-2,4 dodecadionate;
    (b) said solvent is acetone;
    (c) said surfactant is sodium stearoyl-2-lactylate;
    (d) said mixture is heated to 120 degrees Farenheit; and
    (e) the approximate proportions by weight are 1:1:.1:19 of said chemical to said fat to said surfactant to said solvent.

3. A process as described in claim 2 wherein said mixture is pressure injected into said body of water through a 27 gauge needle.

4. A process as described in claim 1 wherein:
    (a) said chemical is 6,7epoxy-3,7-dimethyl-1-[3,4-(methylenedioxy)-phenoxy]-2-nonene;
    (b) said solvent is chloroform;
    (c) said surfactant is sodium stearoyl-2-lactylate; and
    (d) said solvent is removed from said mixture by spray drying and recovered in water by impinger sampling.

5. A process as described in claim 1 wherein said solvent is miscible in water.

6. A process as described in claim 5 wherein the step of removing said solvent comprises pressure injecting said colloid particles into the water through a fine needle to dissolve said solvent and to assure that said colloid particles will be of very small dimension.

* * * * *